United States Patent [19]

Williams

[11] Patent Number: 5,263,976

[45] Date of Patent: Nov. 23, 1993

[54] MOUTH BITE DEVICE

[76] Inventor: James A. Williams, P.O. Box 16577, Beverly Hills, Calif. 90209-2577

[21] Appl. No.: 822,886

[22] Filed: Jan. 21, 1992

[51] Int. Cl.$^5$ ............................................. A61J 17/00
[52] U.S. Cl. ............................................. 606/235; 606/1
[58] Field of Search ............ 433/214; 128/776, 777; 606/1, 108, 234, 236

[56] References Cited

U.S. PATENT DOCUMENTS

| | | | |
|---|---|---|---|
| 403,213 | 5/1889 | Qutman | 604/79 |
| 745,920 | 12/1903 | Spencer | 606/236 |
| 1,023,822 | 4/1912 | Dubay | 606/235 |
| 1,586,499 | 5/1926 | Worth | 606/235 |
| 1,749,632 | 3/1930 | Ferris | 606/234 |
| 2,588,169 | 3/1952 | Shea | 433/214 |
| 2,798,482 | 7/1957 | Fenney | 606/235 |
| 3,129,709 | 4/1964 | Rountree | 606/234 |
| 3,187,746 | 6/1965 | Gerber | 606/235 |
| 3,800,782 | 4/1974 | Josephson et al. | 128/777 |
| 3,924,638 | 12/1975 | Mann | 606/234 |

FOREIGN PATENT DOCUMENTS 3738475 5/1989 Fed. Rep. of Germany ...... 128/777

*Primary Examiner*—Stephen C. Pellegrino
*Assistant Examiner*—Glenn Dawson
*Attorney, Agent, or Firm*—Allan M. Shapiro

[57] ABSTRACT

The mouth bite device includes a handle and a crossbar thereon to form a T-shaped device. The crossbar has resilient sections toward its ends. The device is sized so that the handle can manipulate the crossbar so that the crossbar enters across the mouth and the resilient sections respectively lie between the opposing molars of the user so that, as he bites down, he engages his molars on the resilient sections. This permits the user to clench his teeth without damage, thus relieving tension and releasing emotional energy.

8 Claims, 1 Drawing Sheet

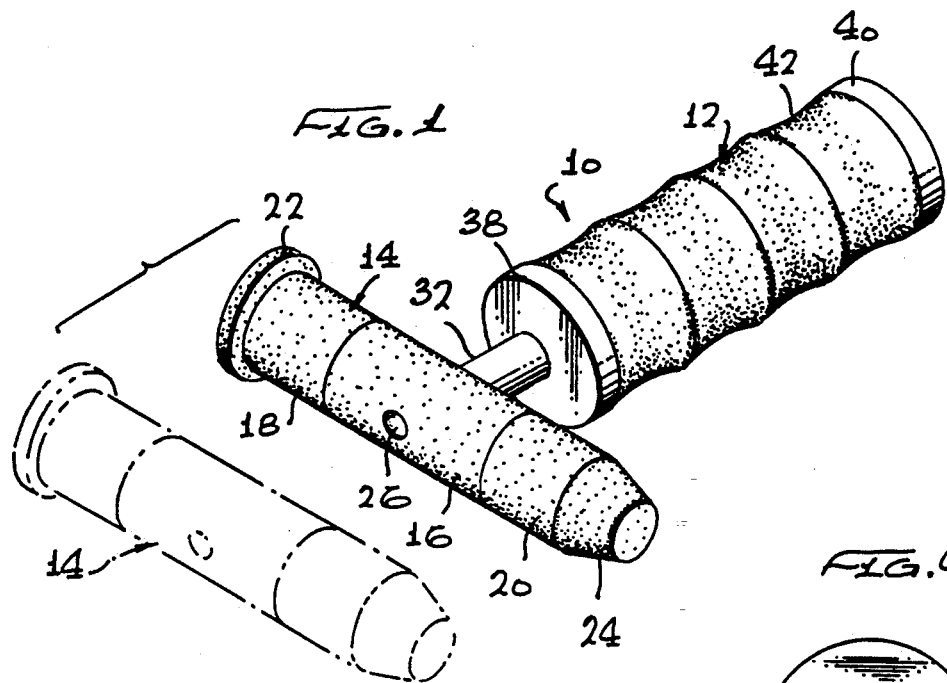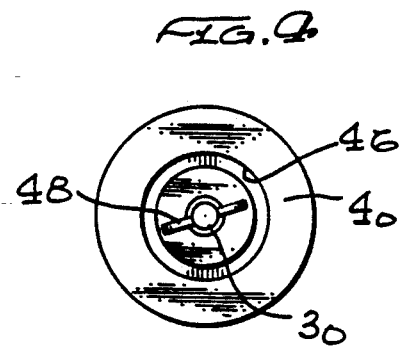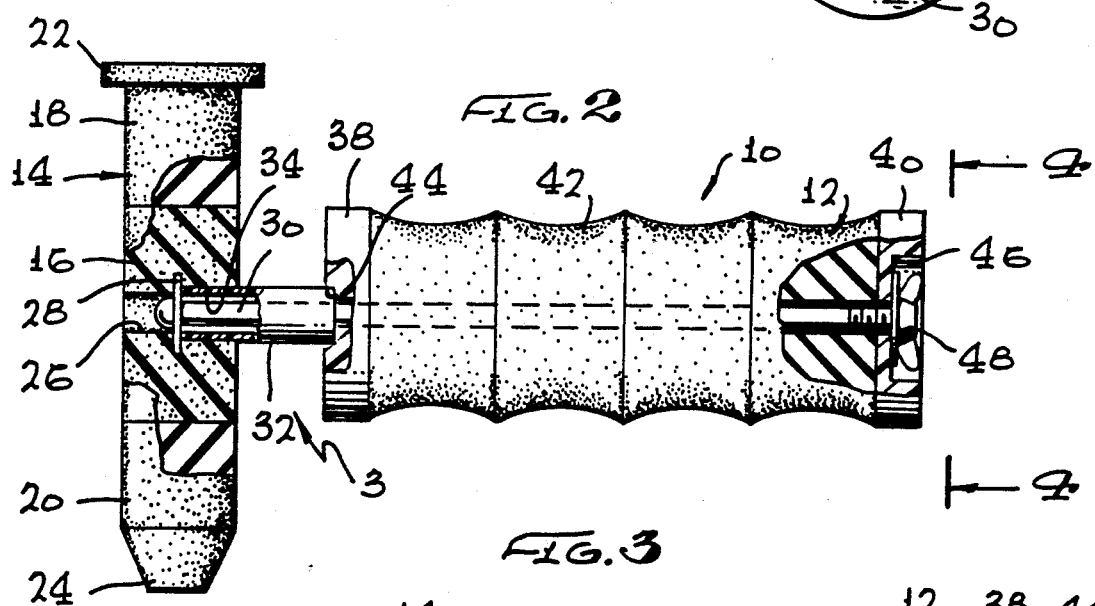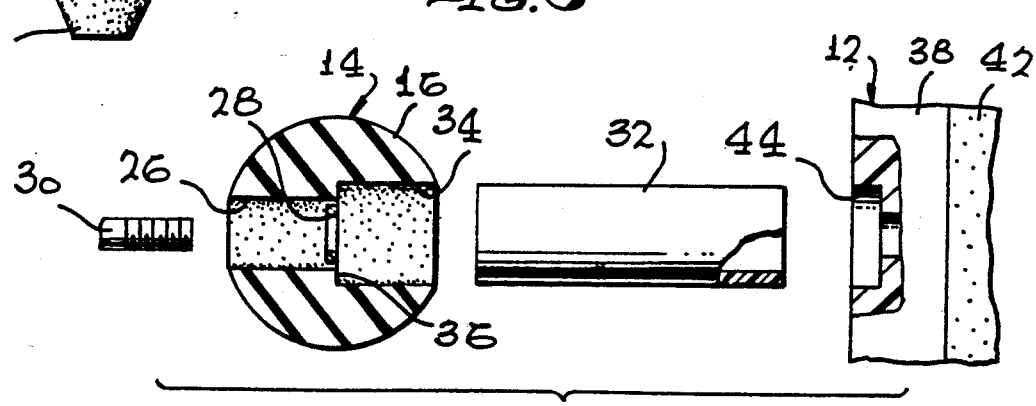

MOUTH BITE DEVICE

FIELD OF THE INVENTION

This invention is directed to a mouth bite device which can be inserted across and held in the mouth of the user so that the user may bite down thereon without hurt to his teeth.

BACKGROUND OF THE INVENTION

When a person is subjected to stress, he must relieve that stress in one way or another. The stress may be physical, such as pain. Pain comes from headaches as well as muscular, joint and nerve problems. Sometimes these pains cannot be eliminated by medication. In these cases, medication significantly reduces the pain, but an outlet is needed to release the buildup of internal tension. In a similar way, psychological stresses resulting from emotional situations need relief. In either case, the release or outlet for the pain or stress must be properly channeled. When it is improperly channeled, it may result in harm to the person or to those around him. It is, therefore, important to channel stress from pain or psychological tension to a proper release.

Electroshock therapy employed for some conditions some years ago resulted in convulsions. These convulsions caused oral and dental damage. As a result, mouth-protecting devices were developed. These devices had the purpose of protecting the patient's teeth, tongue and lips during electroshock convulsions. Several configurations created also included control of the tongue to keep it out of the way of damage from the teeth. Such devices do not satisfy the present function and are of a different configuration.

SUMMARY OF THE INVENTION

In order to aid in the understanding of this invention, it can be stated in essentially summary form that it is directed to a mouth bite device which is useful as an outlet for tension and emotional stress. The mouth bite device has a crossbar with resilient sections toward the ends thereof with those resilient sections being positioned so that they can be engaged between the molars on the opposite sides of the mouth of the user. The user can bite down on the resilient sections to offer a stress and tension release, thus relieving tension and reducing traumatic mental conditions. The crossbar preferably carries a handle for manipulation of the crossbar into place and for holding of the device by the user.

It is thus an object and advantage of this invention to provide a mouth bite device which a person can place in his mouth with resilient sections between his molars so that tension and stress can be relieved by biting on the mouth bite device.

It is another object and advantage of this invention to provide a mouth bite device which is shaped in the form of a T with the crossbar of the T being sized so that it can be placed across the mouth and between the molars on the opposite sides of the mouth, and the upright of the T serves as a handle by which the crossbar is positioned and removed.

It is a further object and advantage of this invention to provide a mouth bite device which has a reusable handle in connection with a throwaway crossbar so that, once used, the crossbar can be disposed of, presumably with teeth marks in the resilient sections thereof, and the handle can be reused.

It is another object and advantage of this invention to provide a mouth bite device which is useful in providing the exit port from the body for relief of excessive physical or mental pain during moments of intense tension, stress or psychological pressure.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is an isometric view of the mouth bite device of this invention, with the crossbar shown in the dashed line removed position.

FIG. 2 is a side-elevational view thereof, with parts broken away and parts taken in section.

FIG. 3 is an enlarged exploded view taken generally in the direction of arrow 3 in FIG. 2.

FIG. 4 is an end view, as seen generally along line 4—4 of FIG. 2.

DESCRIPTION OF THE PREFERRED EMBODIMENT

The mouth bite device of this invention is generally indicated at 10 in FIGS. 1 and 2. The device 10 is generally T-shaped and has a handle 12 and a crossbar 14. The crossbar 14 is sized and configured for insertion into and across the mouth. The crossbar 14 is made of two kinds of material. A more rigid center section 16 carries resilient end sections 18 and 20 thereon. The resilient sections may be separately molded and adhesively attached to the center section, or the entire crossbar 14 may be injection-molded together in one mold with the injection of more resilient material at the end sections. The disc 22 is integrally formed with the resilient section 18 and is of the same material. The tapered nose 24 is integrally formed with the resilient end section 20. The disc and tapered nose are present to give the appearance of a bullet on which the user bites to satisfy the saying "bite the bullet." The length of the crossbar 14 from the tip of the tapered nose to the outer end surface of the disc is longer than the distance across the molars, and preferably is longer than the distance between the cheeks so that the end sections 18 and 20 extend slightly past the cheeks when located at the molars. The resilient end sections 18 and 20 fit between the opposing molars on the opposite sides of the mouth so that the user bites down on the end sections with his molars. The crossbar 14 is manipulated into position by means of the handle 12.

Crossbar 14 has a hole 26 therethrough across one of the diameters at the mid-point of the length of the crossbar. Molded into the crossbar is plate 28 which has a bolt hole therethrough. Handle bolt 30 has a head thereon, as seen in FIG. 2. The head lies against the plate 28, and the bolt 30 extends to the right out of the handle. Spacer tube 32 is a rigid tube which extends into the hole 34, which is larger than and in line with the hole 26. The hole 34 terminates at the back of plate 28. The spacer tube 32 enters into the hole 34 and lies against the shoulder 36, see FIG. 3.

Handle 12 is formed of rigid end plates 38 and 40 with a resilient handle section 42 therebetween. The handle section is sufficiently large in diameter and sufficiently long that it can be manually grasped for manipulation of the mouth bite device 10. As is seen in FIG. 3, both of the rigid end plates 38 and 40 have a hole therethrough to pass the bolt 30 Rigid end plate 38 has a recess 44 therein, see FIG. 3, with a shoulder in the bottom of the recess to receive the end of the spacer tube 32, as seen in FIG. 2. The threaded end of the bolt extends into the recess 46 in end plate 40. Wing nut 48 is threaded onto the bolt 30 to tension the bolt and tighten the structure. A washer may be inserted below the wing nut to spread the load and decrease the friction of tightening the wing nut. Recess 46 is sufficiently large to receive the wing nut so that it is hidden and out of the way. If necessary, the handle bolt 30 may have a slot in the head or may have a square shank together with a square opening through plate 28 to restrain rotation of the bolt 30 during manipulation of the wing nut.

The user manipulates the mouth bite device 10 by grasp of the handle 12. He inserts the crossbar 14 into and across the mouth with the resilient end sections 18 and 20 between the molars and preferably extending laterally out of the mouth past the cheeks so that other people, particularly any health care personnel present, can observe the in mouth conditions of the user. In this position, the rigid end plate 38 of the handle is forward of his lips and incisors. His lips may contact the spacer tube 32, but his incisors are held away from the spacer tube by means of the spacing provided by the resilient end sections 18 and 20 between his molars. Also, the spacer tube 32 is long enough to prevent lip contact with the handle 12. In this position, the user can bite down on the mouth bite device to relieve pain, tension or anxiety. This gives a psychological outlet by channeling stress through the mouth by biting on the mouth bite device 10. This relieves tensions and reduces mental traumatic conditions. It also offers the user the psychological benefit of being able to fight back against the pain or stress.

Since the resilient end sections 18 and 20 of the crossbar 14 are engaged by the teeth, they need to be replaceable. The wing nut 48 is removed, and the bolt 30 is drawn out of the cross piece 12. Normally, the spacer tube 32 also will be discarded after a single use. A new crossbar 14 and spacer tube 32 are provided, possibly from a sterile wrapper, and the bolt 30 is passed therethrough. The crossbar and handle are put into the position shown in FIG. 2, and the wing nut 48 is put in place and tightened so that, if necessary, the device 10 may be sterilized and made ready for another use.

This invention having been described in its preferred embodiment, it is clear that it is subject to numerous modifications, modes and embodiments within the ability of those skilled in the art and without the exercise of the inventive faculty. Accordingly, the scope of this invention is defined by the scope of the following claims.

What is claimed is:

1. A mouth bite device comprising:
   a handle sized to be manually grasped by the user of the mouth bite device; and
   a crossbar on said handle, said crossbar having first and second ends and a cylindrical center section, said crossbar being formed of resilient material adjacent said first and second ends, one of said ends being formed with a bullet-like disc appearance and the other of said ends being formed with a bullet-like tapered nose appearance so that said crossbar resembles a bullet.

2. A mouth bite device comprising:
   a handle sized to be manually grasped by the user of the mouthbite device;
   a crossbar detachably mounted on said handle, said crossbar having a substantially rigid center section and opposite end sections, said end sections being formed of resilient material, one of said end sections being formed with a bullet-like disc appearance and the other of said end sections being formed with a bullet-like tapered nose appearance so that said crossbar resembles a bullet; and
   detachable attachment means in said rigid center section for detachable attachment of said crossbar to said handle.

3. A mouth bite device comprising:
   a handle sized to be manually grasped by the user of the mouthbite device; and
   a crossbar having a cylindrical center section and a pair of opposite end sections, one of said end sections being formed with a bullet-like disc appearance and the other of said end sections being formed with a bullet-like tapered nose appearance so that said crossbar resembles a bullet, said end sections being formed of resilient material, said handle being attached to said crossbar at said center section.

4. A mouth bite device comprising:
   a handle, said handle being sized for manual manipulation by the user of the mouth bite device;
   a crossbar, said crossbar having first and second ends and a substantially rigid center section, said crossbar being resilient adjacent said first and second ends, a plate positioned within said center section; and
   a bolt engaged in both said handle and said plate in said center section for detachably attaching said crossbar to said handle.

5. The mouth bite device of claim 4 further including a spacer tube between said handle and said crossbar, said spacer tube being of such length that the user's lips cannot contact said handle when said resilient sections of said crossbar are engaged by the user's molars.

6. The mouth bite device of claim 5 wherein said bolt for detachably attaching said crossbar to said handle extends through said spacer tube.

7. The mouth bite device of claim 4 wherein said handle comprises substantially rigid end plates and a resilient handle section therebetween.

8. The mouth bite device of claim 7 wherein said end plates and handle section have an opening therethrough and said bolt extends therethrough and said bolt is engaged in one of said end plates.

* * * * *